(12) United States Patent
Nishihara

(10) Patent No.: US 6,361,562 B1
(45) Date of Patent: Mar. 26, 2002

(54) BIOMATERIALS

(76) Inventor: Katsunari Nishihara, 2-7-3, Takadanobaba, Shinjuku-ku, Tokyo 169-0075 (JP)

( * ) Notice: Subject to any disclaimer, the term of this patent is extended or adjusted under 35 U.S.C. 154(b) by 0 days.

(21) Appl. No.: 09/375,244

(22) Filed: Aug. 16, 1999

Related U.S. Application Data

(63) Continuation-in-part of application No. 08/968,023, filed on Nov. 12, 1997, now Pat. No. 5,990,381.

(51) Int. Cl.⁷ .................................................. A61F 2/02
(52) U.S. Cl. ................................. 623/11.11; 623/13.17
(58) Field of Search ........................... 623/11.11, 13.17, 623/66.1; 424/422, 423

(56) References Cited

FOREIGN PATENT DOCUMENTS

| JP | 10216214 A | 8/1998 |
|---|---|---|
| JP | 10263069 A | 10/1998 |

*Primary Examiner*—Dinh X. Nguyen
(74) *Attorney, Agent, or Firm*—Fish & Richardson, P.C.

(57) ABSTRACT

The present invention provide a biomaterial comprising an extirpated piece from a tissue selected from the group consisting of the cornea, muscle, tendon, cartilage, alimentary canal, liver, pancreas, spleen, kidney, heart, blood vessel, nerve and brain of Chondrichthyes, Osteichthyes or Cyclostomata.

5 Claims, No Drawings

BIOMATERIALS

CROSS-REFERENCE TO RELATED APPLICATIONS

This application is a Continuation-in-Part of U.S. patent application Ser. No. ("USSN") 08/968,023, filed Nov. 12, 1997, which issued as U.S. Pat. No. 5,990,381 on Nov. 23, 1999; and claims priority to Japanese Application No. 72041/1997, filed Mar. 25, 1997; and Japanese Application No. 311979/1997, filed Nov. 13, 1997. Each of the aforementioned applications and patent are explicitly incorporated herein by reference in their entirety and for all purposes.

FIELD OF THE INVENTION

The present invention relates to biomaterials comprising an extirpated piece from Chondrichthyes, Osteichthyes or Cyclostomata. More specifically, the present invention relates to biomaterials that comprise the above extirpated piece and are applicable as various alternative organs and implant materials.

BACKGROUND OF THE INVENTION

It has been considered difficult to achieve a successful xenogeneic transplantation between different kinds of animal in view of major histocompatibility complex (MHC) which causes the rejection reaction in the transplantation.

OBJECTS AND SUMMARY OF THE INVENTION

The inventor of the present invention has found that although a primitive vertebrate including Chondrichthyes, Cyclostomata and a part of Osteichthyes has a gene encoding MHC, the primitive vertebrate is in a state of immunological tolerance as seen in an embryo of a higher animal. The difference between the primitive vertebrate and the higher animal may be explained as follows: the expression of MHC gene was induced by an increased blood pressure caused in response to the gravity during the second revolution of vertebrates in the evolutionary process (i.e. terrestrialization), thereby generating human leukocyte antigen (HLA) in the course of evolution. As a result, the rejection reaction can be caused in the xenogeneic transplantation.

The inventor also has found that a skin transplantation between sharks as well as between shark and Cyclostomata can be successfully carried out, which had been considered impossible for a long time. In addition, it is also possible to transplant various organs from sharks to mammals.

The sharks have a much lower blood pressure whereas the mammals have a higher one because the sharks, in which the gravity is offset by buoyancy, differ from the mammals in responding to the gravity. Various organs from the shark may be transplanted to the mammals without any need for angiorrhaphy.

A series of studies shows that a primitive vertebrate is composed of the proteins that are closely similar to fetal proteins of the mammals. Various tissues from the primitive vertebrate have been observed to smoothly replace the mammal's own tissues after transplantation.

In the case of human, a successful transplantation has been achieved only with allograft of organs between a recipient and a donor compatible with the recipient in histocompatibility antigen. According to the present invention, it is possible to use various tissues from the primitive vertebrate (e.g. viscus, nerve and cornea) for transplantation in human, so that an important contribution can be made to the progress of medical science.

The present application encompasses the following inventions:

(1) A biomaterial comprising an extirpated piece from a tissue selected from the group consisting of the cornea, muscle, tendon, cartilage, alimentary canal, liver, pancreas, spleen, kidney, heart, blood vessel, nerve and brain of Chondrichthyes, Osteichthyes or Cyclostomata;

(2) The biomaterial according to (1), wherein the extirpated piece is obtained from a tissue of Chondrichthyes or Osteichthyes;

(3) The biomaterial according to (1), wherein the extirpated piece is obtained from a tissue of Chondrichthyes;

(4) The biomaterial according to (1), which is transplanted into mammals; and (5) The biomaterial according to (1), which is selected from the group consisting of an artificial cornea, an artificial muscle tissue, an artificial tendon, an artificial cartilage, an artificial alimentary canal tissue, an artificial liver tissue, an artificial pancreas tissue, an artificial spleen tissue, an artificial kidney tissue, an artificial heart tissue, an artificial blood vessel, an artificial nerve tissue and an artificial brain tissue.

DETAILED DESCRIPTION OF THE INVENTION

Fishes to be used for obtaining an extirpated piece for preparing the biomaterials of the present invention may be Chondrichthyes, Osteichthyes or Cyclostomata.

As Chondrichthyes, fishes belonging to Elasmobranchii such as sharks and rays are preferred. Among all, sharks are most preferred. Specific examples of sharks include Shirozame, Mustelus, Triakis (dochizame) and Heterodontus(nekozame). Specific examples of rays include Anacanthobatis, Dasyatis and Pristis.

The Osteichthyes includes fishes having an endoskeleton, at least a part of which is bony, and a skull coated with periosteum. Fishes belonging to the Osteichthyes are roughly divided into large fishes and small fishes. Specific examples of large Osteichthyes include tuna, bonito and sea bass. Specific examples of small Osteichthyes include salmons such as Shirozake; sea breams such as Pagrus and Oplegnathus; red snappers such as Beryx and Anomalops; flatfishes such as Limanda and Engyprosopon; Seriola (yellowtail and young yellowtail) or Clupea.

The Cyclostomata includes fishes belonging to Agnatha including Petromyzontiformes and Myxiniformes. Specific examples include Lampetra japonica, Myxine and Eptatretus.

The extirpated piece used for preparing the biomaterials of the present invention may be taken from the following tissues or organs of these fishes: cornea, muscle, tendon, cartilage, alimentary canal, liver, pancreas, spleen, kidney, heart, blood vessel, nerve and brain.

The cornea used for the present invention may be taken from one or both of eyes of the Chondrichthyes and Osteichthyes (small one), and transplanted to each eye of mammals. A muscle used for the present invention may be, for example, a dorsal muscle of the Chondrichthyes. A tendon used for the present invention may be, for example, a fin of the Chondrichthyes. A cartilage used for the present invention may be, for example, a vertebral cartilage of the Chondrichthyes or an intervertebral cartilage of the Osteichthyes (large one). As an alimentary canal used for the present invention, for example, a part from the stomach to intestine may be used. In the case of the liver, for example, a hepatic parenchymal tissue from the Chondrichthyes may be implanted into the mammal's liver including the human liver by incision. In the case of the pancreas, for example, the pancreas from the Chondrichthyes may be implanted into the mammal's spleen or pancreas by incision. In the case of the spleen, for example, the spleen from the Chondrichthyes or Osteichthyes may be implanted into the spleen of a patient affected with blood disease by incision. In the case of the kidneys, for example, one or both of the kidneys from the Chondrichthyes may be implanted into a mammal's renal parenchymal tissue by incision. In the case of the heart, the recipient's heart from which a damaged part has been removed may be covered and sewn with the heart, for example, from the large Osteichthyes or Chondrichthyes. In the case of a nerve or the brain, the spinal cord from the Cyclostomata or Chondrichthyes may be transplanted as an alternative to nerve, or the brain from the Chondrichthyes may be transplanted to mammals. As an alternative to a blood vessel, for example, the alimentary canal from the Chondrichthyes or Cyclostomata may be used, from which an inner epithelial mucosa has been removed and which is turned over before used.

These extirpated pieces from the Chondrichthyes, Osteichthyes and Cyclostomata are preferred because there is no blood group substance or major histocompatibility antigen (i.e. no antigenicity) in these extirpated pieces including the cornea, muscle, tendon, cartilage, alimentary canal, liver, pancreas, spleen, kidney, heart, blood vessel, nerve and brain.

The biomaterials of the present invention may be used as an artificial tissue or organ including an artificial cornea, an artificial muscle tissue, an artificial tendon, an artificial cartilage, an artificial alimentary canal tissue, an artificial liver tissue, an artificial pancreas tissue, an artificial spleen tissue, an artificial kidney tissue, an artificial heart tissue, an artificial blood vessel, an artificial nerve tissue and an artificial brain tissue.

The term "artificial tissue or organ" used here refers to a tissue or organ derived from organisms that can be used as an alternative to at least a part of a tissue or organ in a transplant recipient.

In the case of the artificial cornea, the cornea of Chondrichthyes (e.g. shark) or a small Osteichthyes can be used as an alternative to a mammalian denatured cornea. In the case of the artificial muscle tissue, a dorsal muscle of Chondrichthyes (e.g. shark) or Cyclostomata can be used for replacing an injured muscle, filling a defect in muscles or augmenting a muscle in mammals. In the case of the artificial tendon, a tendon of a fin taken from a fish can be used for replacing an injured tendon in mammals. In the case of the artificial cartilage, a vertebral or intervertebral cartilage taken from a fish can be used for replacing an injured joint cartilage in mammals. The alimentary canal from the stomach to intestine may be used as the artificial alimentary canal tissue (e.g. an artificial esophagus) or an alternative to trachea. Although the livers of Chondrichthyes, Osteichthyes and Cyclostomata differ from the human liver in types of metabolic isozyme, they may be used as the artificial liver tissue without any problem on detoxication. The artificial pancreas tissue may be used for producing insulin by direct implantation of a fish-derived pancreatic parenchymal tissue including Langerhans' islands into a hemostatically cut opened-pocket in a mammalian recipient's pancreas. In the case of the artificial spleen tissue, a splenic parenchymal tissue taken from a fish may be cut into 1 cm cubes and implanted into a hemostatically cut opened-pocket in a mammalian recipient's spleen. In the case of the artificial liver or pancreas, a hepatic or pancreatic parenchymal tissue taken from a fish may be similarly cut into 1 cm cubes and implanted into a hemostatically cut opened-pocket in a mammalian recipient's liver or pancreas. In the case of the artificial kidney tissue, a renal parenchymal tissue taken from a fish may be similarly cut into 0.5 cm cubes and implanted into a hemostatically cut opened-pocket in a mammalian recipient's kidney. In the case of the artificial heart tissue, a heart tissue taken from a fish may be shaped into a 2 cm square and sewn to a mammalian recipient's heart from which necrosed muscles have been removed. As the artificial blood vessel, an aorta of a fish may be used for transplantation. In the case of a nerve, the spinal cord of the Cyclostomata has a length of about 20 cm and may be used as the artificial nerve tissue to replace a broken nerve. In the case of the artificial brain tissue, a brain tissue taken from a fish may be cut into 3 mm cubes and implanted into a mammalian recipient's head in which a part of the brain has been injured, necrosed or lost. The alimentary canal may also be used as the artificial blood vessel, from which an intima has been removed and which is turned over before used.

The artificial cornea, artificial muscle tissue, artificial tendon, artificial cartilage, artificial alimentary canal tissue, artificial liver tissue, artificial pancreas tissue, artificial spleen tissue, artificial kidney tissue, artificial heart tissue, artificial blood vessel, artificial nerve tissue and artificial brain tissue thus obtained can be rapidly fused with living tissues because of its non-antigenicity without HLA (human leukocyte antigen), and therefore, a scar will not be prominent.

The biomaterials of the present invention can be subjected to a sterilization process by cooling at −60° C., washing with saline, washing with a saline solution containing an antibiotic and then soaking them in recipient's blood after being shaped into a suitable shape used as the artificial cornea, artificial muscle tissue, artificial tendon, artificial cartilage, artificial alimentary canal tissue, artificial liver tissue, artificial pancreas tissue, artificial spleen tissue, artificial kidney tissue, artificial heart tissue, artificial blood vessel, artificial nerve tissue, artificial brain tissue, and the like. They can also be stored aseptically at a low temperature. Accordingly, the biomaterials of the present invention are also preferable in view of these aspects.

The biomaterials of the present invention have a prolonged storage life of about 6 months in saline or seawater at −60° C. Accordingly, the biomaterials of the present invention can be sufficiently provide when there is a sudden need for them.

Unlike the conventional materials derived from bovine or human, the biomaterials of the present invention have no risk of viral infection and are stably provided. They are the preferred alternatives to the above conventional biomaterials and transplantable organs.

DESCRIPTION OF THE PREFERRED EMBODIMENT

Hereinbelow, the present invention will be described more specifically with reference to the following Examples, which are not intended to limit the scope of the present invention.

EXAMPLE 1

The intestine was taken from Triakis and then washed with a saline solution containing an antibiotic of broad spectrum. It was soaked in a saline solution containing an antibiotic (gentamicin) for 10 minutes. This intestine in a tubular form was cut into 2 cm lengths. It was then soaked in two sterilized dishes containing blood (50 ml) of an adult recipient dog for 10 minutes respectively before being transplanted into the dog. The small intestine of the dog was cut and the intestine of Triakis having a length of 2 cm was inserted thereinto and sewn up trebly at both ends. After the operation, an antibiotic (amoxicillin) was injected into the dog drip-wise. The intestine of Triakis was transplanted into the dog's intestine successfully without mesenteritis. In this example, two dogs were subjected to the transplantation. The transplanted intestines were removed from the dogs after one and tree months to observe that these intestines were transplanted successfully without any rejection. The histological findings of specimens of these intestines showed a normal intestinal canal mucosa having a high content of goblet cells, which is characteristic of fishes. The protein composition of primitive vertebrates is identical with that of fetal mammals without HLA. The proteins of primitive vertebrate are therefore considered to be replaced with proteins in adult mammals.

In the case of the liver, pancreas, spleen and kidney, each of their parenchymal organs was cut into 5 mm cubes and two pieces of each kind of them were hemostatically transplanted into each of two adult dogs (40 kg, German shepherd). Each organ of these dogs, which underwent the transplantation, was cut opened hemostatically using an ultrasonic scalpel. These transplanted organs were observed to have replaced the dog's own tissues without any rejection.

EXAMPLE 2

The brain of Eptatretus having a body length of 40–50 cm was opened. Its medulla oblongata was cut opened by about 1 cm to pull out its backbone. The spinal cord was removed from the backbone to obtain a nerve tissue having a size of 0.5×10 cm. This nerve tissue was cut into 10 pieces of 1 cm in length and these pieces were then subcutaneously implanted into each of mammals such as mouse, rat or chicken.

After 24 hrs, 48 hrs, 96 hrs, 14 days and three months, the implanted tissues were taken from the mammals and histopathologically observed. Simultaneously, the form of nerve cells was also observed.

There was no particular reaction (e.g. inflammation) nor rejection observed between the implanted nerve cells and their surrounding tissue. The form of nerve cells was maintained for at least three months after the implantation.

It is therefore revealed that the nerve tissue from Eptatretus can be used as an artificial nerve.

EXAMPLE 3

Two nerves from Eptatretus were cut into 0.5–1 cm length and transplanted into a mouse whose three femoral nerves had been cut off by 0.5 cm. After one week of the transplantation, its hind legs started to move.

EXAMPLE 4

The head of Triakis was opened using a trephine (1 cm in diameter) to obtain a 3 mm cube of brain tissue. The cranial bone of a rat was opened using a trephine (5 mm in diameter) to remove a 3 mm cube of brain tissue, and the brain tissue taken from Triakis was implanted thereinto. After the implantation, the cranial bone of the rat was closed. No change was observed in the rat's behavior. A histological specimen was prepared after three months of the implantation. In this example, eight rats were subjected to the implantation. The brain tissue from Triakis was observed to have been successfully implanted into all the rats without any rejection.

EXAMPLE 5

Eight dorsal muscles having a size of 1 cm×1 cm×2 cm were taken from Triakis. These muscles were then transplanted into dorsal muscles of each of three adult dogs (German shepherd). After two, three and four months of the transplantation, the transplanted muscles were removed from the dogs to prepare histological specimens. All the muscles from Triakis were observed to have been successfully transplanted into the dogs without any rejection.

EXAMPLE 6

Eight vertebral cartilages having a size of 1 cm×1 cm×2 cm were taken from Triakis. These cartilages were then transplanted into dorsal muscles of each of three adult dogs (German shepherd). All the transplanted cartilages were observed to have been successfully fused with their surrounding tissues in the dogs while partially ossifying in the muscles.

EXAMPLE 7

A fin having a size of 1 cm×1 cm×2 cm was taken from Triakis. The fin was cut into eight slices for using each slice as an artificial tendon. These tendons were then transplanted into dorsal muscles of each of three adult dogs (German shepherd). All the tendons from Triakis were observed to have been successfully transplanted into the dogs without any change.

EXAMPLE 8

A full-thickness cornea was taken from Triakis and transplanted into an eye of a dog (beagle) from which half the thickness of its cornea had been removed. The cornea from Triakis was observed to have been successfully fused with the dog's own cornea. The eye of the dog was observed to keep its function normal.

EXAMPLE 9

A full-thickness cornea in a round shape was taken from Triakis using a trephine for corneal transplantation in human, and then transplanted to an eye of a dog (beagle) from which a full-thickness cornea had been roundly removed using a trephine for corneal transplantation in human. The cornea taken from Triakis was sewn to the remaining cornea of the dog with a very fine surgical suture used for corneal transplantation in human. The upper and lower eyelids of the dog were sewn up with a thick surgical suture in order to stabilize the transplanted cornea. After two weeks, the surgical suture between the upper and lower eyelids was removed to find that the transplanted cornea had been successfully fused with the dog's own cornea.

All publications, patents and patent applications cited here are incorporated here by reference in their entirely.

What is claimed is:

1. A biomaterial comprising a sterilized extirpated piece from a tissue selected from the group consisting of a cornea, a muscle, a tendon, a cartilage, an alimentary canal, a liver, a pancreas, a spleen, a kidney, a heart, a blood vessel, a nerve, and a brain of Chondrichthyes, Osteichthyes or Cyclostomata.

2. The biomaterial according to claim 1, wherein the extirpated piece is obtained from a tissue of Chondrichthyes or Osteichthyes.

3. The biomaterial according to claim 1, wherein the extirpated piece is obtained from a tissue of Chondrichthyes.

4. The biomaterial according to claim 1, which is transplanted into mammals.

5. The biomaterial according to claim 1, which is selected from the group consisting of an artificial cornea, an artificial muscle tissue, an artificial tendon, an artificial cartilage, an artificial alimentary canal tissue, an artificial liver tissue, an artificial pancreas tissue, an artificial spleen tissue, an artificial kidney tissue, an artificial heart tissue, an artificial blood vessel, an artificial nerve tissue and an artificial brain tissue.

\* \* \* \* \*